(12) United States Patent
Douglas et al.

(10) Patent No.: US 9,632,068 B2
(45) Date of Patent: Apr. 25, 2017

(54) SETTING ATMOSPHERIC CONDITIONS FOR A TEST COMPUTING DEVICE

(71) Applicant: Oracle International Corporation, Redwood City, CA (US)

(72) Inventors: David Douglas, Palo Alto, CA (US); Anthony Eberhardt, Los Gatos, CA (US); Henry Bono, San Jose, CA (US); Yuan Gao, Sunnyvale, CA (US)

(73) Assignee: Oracle International Corporation, Redwood Shores, CA (US)

( * ) Notice: Subject to any disclaimer, the term of this patent is extended or adjusted under 35 U.S.C. 154(b) by 402 days.

(21) Appl. No.: 14/315,253

(22) Filed: Jun. 25, 2014

(65) Prior Publication Data

US 2015/0377534 A1    Dec. 31, 2015

(51) Int. Cl.
*F25B 49/00* (2006.01)
*G01N 33/00* (2006.01)

(52) U.S. Cl.
CPC ..... *G01N 33/0016* (2013.01); *G01N 33/0073* (2013.01)

(58) Field of Classification Search
CPC . G06F 1/20; G06F 2200/201; H05K 7/20736; H05K 7/20745; H05K 7/20827; H05K 7/20836; F24F 11/0012; F24F 11/008; F24F 13/02; F24F 13/08; F24F 2011/0041; F24F 2011/0042; F24F 3/00; F24F 11/00; F24F 13/00; G01N 33/0016; G01N 33/0073; F25B 49/00
See application file for complete search history.

(56) References Cited

U.S. PATENT DOCUMENTS

2007/0074525 A1* 4/2007 Vinson ............... H05K 7/20745
62/259.2

OTHER PUBLICATIONS

"Power and cooling technologies in the HP POD 240a"; www.hp.com/go/pod240a; Copyright 2012 Hewlett-Packard Development Company, LP. (8 pages).
Atwood, Don, et al., "Reducing Data Center Cost with an Air Economizer", Intel Corporation, Aug. 2008, (4 pages).
Evans, Tony, "The Different Types of Air Conditioning Equipment for IT Environments", White Paper #59, Rev 2004-0, American Power Conversion. 2004 (21 pages).

* cited by examiner

*Primary Examiner* — Daniel S Larkin
(74) *Attorney, Agent, or Firm* — Osha Liang LLP

(57) ABSTRACT

A system for controlling an atmospheric condition. The system includes: an exhaust conduit, external to a first test computing device, configured to channel exhaust from the first test computing device. Further, the system includes a primary atmospheric conditioner, external to the first test computing device, configured to generate test air comprising the atmospheric condition for the first test computing device by modifying the exhaust. Further still, the system also includes an intake conduit, external to the first test computing device, configured to channel the test air to the first test computing device.

20 Claims, 4 Drawing Sheets

US 9,632,068 B2

SETTING ATMOSPHERIC CONDITIONS FOR A TEST COMPUTING DEVICE

CROSS-REFERENCE TO RELATED APPLICATIONS

The subject matter of the present application may be related to the subject matter of U.S. patent application Ser. No. 14/315,256, filed on Jun. 25, 2014, and entitled: "MANAGING ATMOSPHERIC CONDITIONS OF A TEST COMPUTING DEVICE."

BACKGROUND

In the field of networking, testing of network devices, such as servers, in different operational environments with varying atmospheric conditions may be conducted in temperature controlled rooms, including data centers, chambers, and wind tunnels. Creating the environmental test or operating conditions in the temperature controlled rooms is typically expensive.

SUMMARY

In general, in one aspect, the invention relates to a system for controlling an atmospheric condition. The system comprises: an exhaust conduit, external to a first test computing device, configured to channel exhaust from the first test computing device; a primary atmospheric conditioner, external to the first test computing device, configured to generate test air comprising the atmospheric condition for the first test computing device by modifying the exhaust; and an intake conduit, external to the first test computing device, configured to channel the test air to the first test computing device.

In general, in one aspect, the invention relates to a system for controlling an atmospheric condition. The system comprises: a plurality of production computing devices in a room; a first test computing device in the room; an exhaust conduit, external to the first test computing device, configured to: channel exhaust from the first test computing device; and environmentally separate the plurality of production computing devices from the exhaust of the first test computing device; a primary atmospheric conditioner, external to the first test computing device and the plurality of production computing devices, configured to generate test air comprising the atmospheric condition for the first test computing device by modifying the exhaust; and an intake conduit, external to the first test computing device, configured to: channel the test air to the first test computing device; and environmentally separate the plurality of production computing devices from the test air.

In general, in one aspect, the invention relates to a method for controlling an atmospheric condition. The method comprises: channeling, by an exhaust conduit external to a first test computing device, exhaust from the first test computing device; generating, by a primary atmospheric conditioner external to the first test computing device, test air comprising the atmospheric condition by modifying the exhaust; and channeling, by an intake conduit external to the first test computing device, the test air to the first test computing device.

Other aspects of the invention will be apparent from the following description and the appended claims.

DETAILED DESCRIPTION

Figure 1:
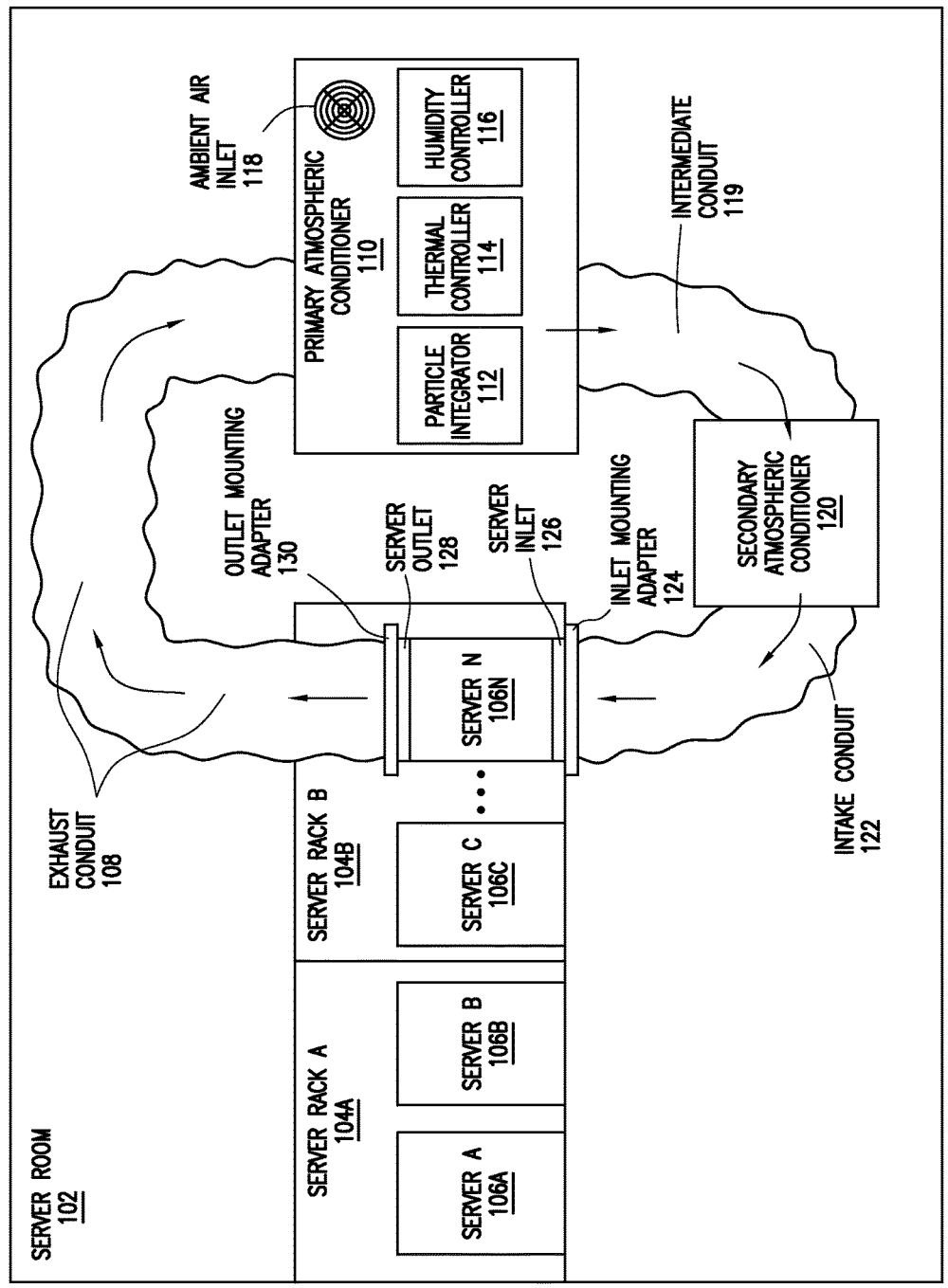
FIG. 1 shows a system for setting/controlling atmospheric conditions for a test computing device in a facility also having a production computing device(s) in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention provide a method and system for setting/controlling atmospheric conditions for a test computing device. Specifically, an exhaust conduit channels the exhaust of the test computing device to one or more atmospheric conditioners. The atmospheric conditioner(s) generate test air having the desired atmospheric conditions (e.g., temperature, moisture, pressure, chemical content, etc.) by modifying the exhaust. The test air is then fed/returned to the test computing device by an intake conduit. The test computing device may be located in the same facility (e.g., server room or any room having a computing device(s)) as other computing devices. The exhaust conduit, the intake conduit, and the atmospheric conditioner(s) environmentally separately (e.g., thermally isolate) the other computing devices from the generated test air and the exhaust. Accordingly, the other computing devices can remain in the same facility as the test computing device and operate normally even though the test computing device is being subjected to test air. In general, the methods/systems for controlling the test environment may also be applied to operating environments.

FIG. 1 shows a system in accordance with one or more embodiments of the invention. As shown in FIG. 1, there exists a server room (102). The server room (102) includes one or more server racks (e.g., server rack A (104A), server rack B (104B)). Each server rack (104A, 104B) is a shelf configured to mount one or more servers. For example, server rack A (104A) mounts server A (106A) and server B (106), while server rack B (104B) mounts server C (106C) and server N (106N). Two server racks may be kept in close proximity to each other or may even be connected. For example, server rack A (104A) is connected to server rack B (104B).

In one or more embodiments of the invention, a server is any type of physical system that includes persistent storage (e.g., hard disk), memory (e.g., Random Access Memory), one or more processors, and one or more network interfaces (not shown). In one or more embodiments of the invention, a processor may be an integrated circuit for processing instructions. For example, the processor(s) may be one or more cores, or micro-cores of a processor. In one or more embodiments of the invention, a network interface on a server is the medium through which communication of data to another network interface on a network device (e.g., server, switch, and router) is possible.

In FIG. 1, server N (106N) is a test computing device. In other words, server N (106N) is being subjected to test air that has different atmospheric conditions (e.g., temperature, pressure, humidity, oxygen content, dust particles, etc.) than the air of the server room (102). The performance of server N (106N) is being observed, measured, evaluated, etc. while being exposed to the test air. Server A (106A), server B (106B), and server C (106C) are not under test and may be operating normally while exposed to the air of the server room (102). Accordingly, each of server A (106A), server B (106B), and server C (106C) may be referred to as a production computing device.

Still referring to FIG. 1, server N (106N) includes a server outlet (128) and a server inlet (126). The server outlet (128) expels exhaust from server N (106N). Server N (106N) may include one or more fans to expel exhaust from server N (106N) through the server outlet (128). The server inlet (126) is a portal through which air flows into the server. Server N (106N) may include one or more fans to draw air into server N (106N). The server inlet (126) and the server outlet (128) may correspond to vents, grates, or openings in the case/shell of server N (106N).

In one or more embodiments of the invention, there exists a primary atmospheric conditioner (110). The primary atmospheric conditioner (110) includes a user interface that allow users (i.e., server testers, network administrators, lab technicians, etc.) to select (i.e., set, input, program, specify, etc.) the desired atmospheric conditions of the test air for server N (106N). For example, using the user interface, the test air may be set to 40° F. with 25% humidity. The primary atmospheric conditioner (110) is configured to generate test air with the selected atmospheric conditions using the exhaust of server N (106N). Specifically, the primary atmospheric conditioner (110) controls/modifies the atmospheric conditions (e.g., temperature, moisture, pressure, chemical composition, etc.) of the exhaust to generate the test air with the selected atmospheric conditions. In other words, the primary atmospheric conditioner (110) transforms the exhaust into the desired test air.

The primary atmospheric conditioner (110) may include an ambient air inlet (118), a particle integrator (112), a thermal controller (114), and a humidity controller (116). In one or more embodiments of the invention, the primary atmospheric conditioner (110) may include additional modules to modify atmospheric conditions of the exhaust to generate test air. For example, a gas module (not shown) may decrease the oxygen content and increase the nitrogen content of the exhaust to generate test air that mimics atmospheric conditions at a high altitude.

In one or more embodiments of the invention, the ambient air inlet (118) is an opening in the primary atmospheric conditioner (110) that intakes ambient air from the server room (102) to mix with the exhaust. For example, the ambient air inlet (118) may correspond to a fan or vent that allows ambient air to enter the primary atmospheric conditioner (110), but does not allow test air to exit the primary atmospheric conditioner (110). In one or more embodiments of the invention, the primary atmospheric conditioner (110) includes one or more exhaust vents (not shown) to expel excess air. The primary atmospheric conditioner (110) may also include filters (not shown) to remove dust from the excess air before it is expelled.

In one or more embodiments of the invention, the particle integrator (112) is any combination of hardware and/or software that includes functionality to introduce dust particles into the exhaust. For example, the particle integrator may correspond to a vent through which dust particles may be added by a user (e.g., server tester and network administrator). As another example, the particle integrator may correspond to a container of dust that automatically dispenses dust particles to the exhaust. In one or more embodiments of the invention, any type of particle may be introduced into the exhaust by the primary atmospheric conditioner (110). Examples of particles include sand, clay, silt, salt, etc.

In one or more embodiments of the invention, the thermal controller (114) is any combination of hardware and/or software that includes functionality to modify the temperature of the exhaust. For example, the thermal controller may include an air conditioner to cool the exhaust or a heater to heat the exhaust. The thermal controller may include a thermometer to measure the exhaust at any stage as it is transformed into the test air. In one or more embodiments of the invention, the thermal controller (114) may include functionality to trigger intake of ambient air by the ambient air inlet (118) to cool the exhaust.

In one or more embodiments of the invention, the humidity controller (116) is any combination of hardware and/or software that includes functionality to modify (e.g., increase or decrease) the moisture content of the exhaust. In one or more embodiments of the invention, the humidity controller (116) corresponds to a system that increases moisture content of the exhaust. For example, a humidifier may be used to add and maintain a set percentage for the moisture content. In one or more embodiments of the invention, the humidity controller (116) corresponds to a system that decreases moisture content of the exhaust. For example, a dehumidifier may be used to remove moisture and maintain a set percentage for the moisture content.

In one or more embodiments of the invention, the primary atmospheric conditioner (110) is connected to the server outlet (128) by an exhaust conduit (108) and an outlet mounting adapter (130). The exhaust conduit (108) is effectively a tube, having any type/size of cross-section, that channels the exhaust expelled by server N (106N) to the primary atmospheric conditioner (110). The exhaust conduit may be constructed with any type of material that environmentally separates the exhaust from the server room (102) and the other servers (e.g., server A (106A), server B (106B), and server C (106C)). The outlet mounting adapter (130) connects the exhaust conduit (108) to the server outlet (128). For example, the outlet mounting adapter may correspond to an adhesive, such as tape or glue that attaches the exhaust conduit (108) directly to the server outlet (128). The outlet mounting adapter may be an interface that connects the shape/size of the exhaust conduit (108) with the shape/size of the server outlet (128).

In one or more embodiments of the invention, the test air generated by the atmospheric conditioner(s) is delivered to server N (106N) by an intake conduit (122) and an inlet mounting adapter (124). The intake conduit (122) is effectively a tube, having any type/size of cross-section, that channels the generated test air to server N (106N). The intake conduit (122) may be constructed with any type of material that environmentally separates the test air from the server room (102) and the other servers (e.g., server A (106A), server B (106B), and server C (106C)). The inlet mounting adapter (124) connects the intake conduit (122) to the server inlet (126). For example, the inlet mounting adapter (124) may correspond to an adhesive, such as tape or glue that attaches the intake conduit (122) directly to the server inlet (126). The inlet mounting adapter (124) may be an interface that connects the shape/size of the intake conduit (122) with the shape/size of the server inlet (126).

In one or more embodiments of the invention, there also exists a secondary atmospheric conditioner (120). The secondary atmospheric conditioner (120) is configured to modify the test air before it is channeled to server N (106N). The secondary atmospheric conditioner (120) may have the same functionality as the primary atmospheric conditioner (110). Additionally or alternatively, the secondary atmospheric conditioner (120) has less functionality or different functionality than the primary atmospheric conditioner (110). The secondary atmospheric conditioner (120) may include one or more fans to accelerate/move the generated test air. In one or more embodiments of the invention, the secondary atmospheric conditioner (120) is optional. However, when the secondary atmospheric conditioner (120) is present, it is connected to the primary atmospheric conditioner (110) by an intermediate conduit (119). Like the exhaust conduit (108) and the intake conduit (122), the intermediate conduit (119) may be constructed using any material and may have any size/type of cross section. The intermediate conduit (119) environmentally separates the test air from the air of the server room (102) and the other servers (106A, 106B, 106C).

While FIG. 1 shows a configuration of components, other configurations may be used without departing from the scope of the invention. For example, various components may be combined to create a single component. As another example, the functionality performed by a single component may be performed by two or more components. Moreover, although embodiments of the invention have focused heavily on severs (106A-106N), those skilled in the art, having the benefit of this detailed description, will appreciate that any type of computing device (e.g., personal computer (PC), laptop, mainframe, smart phone, personal digital assistant, cable box, kiosk, printer, tablet PC, e-reader, monitor, fax machine, copier, oscilloscope, electronic test instrument, etc.) may also be used.

Figure 2:
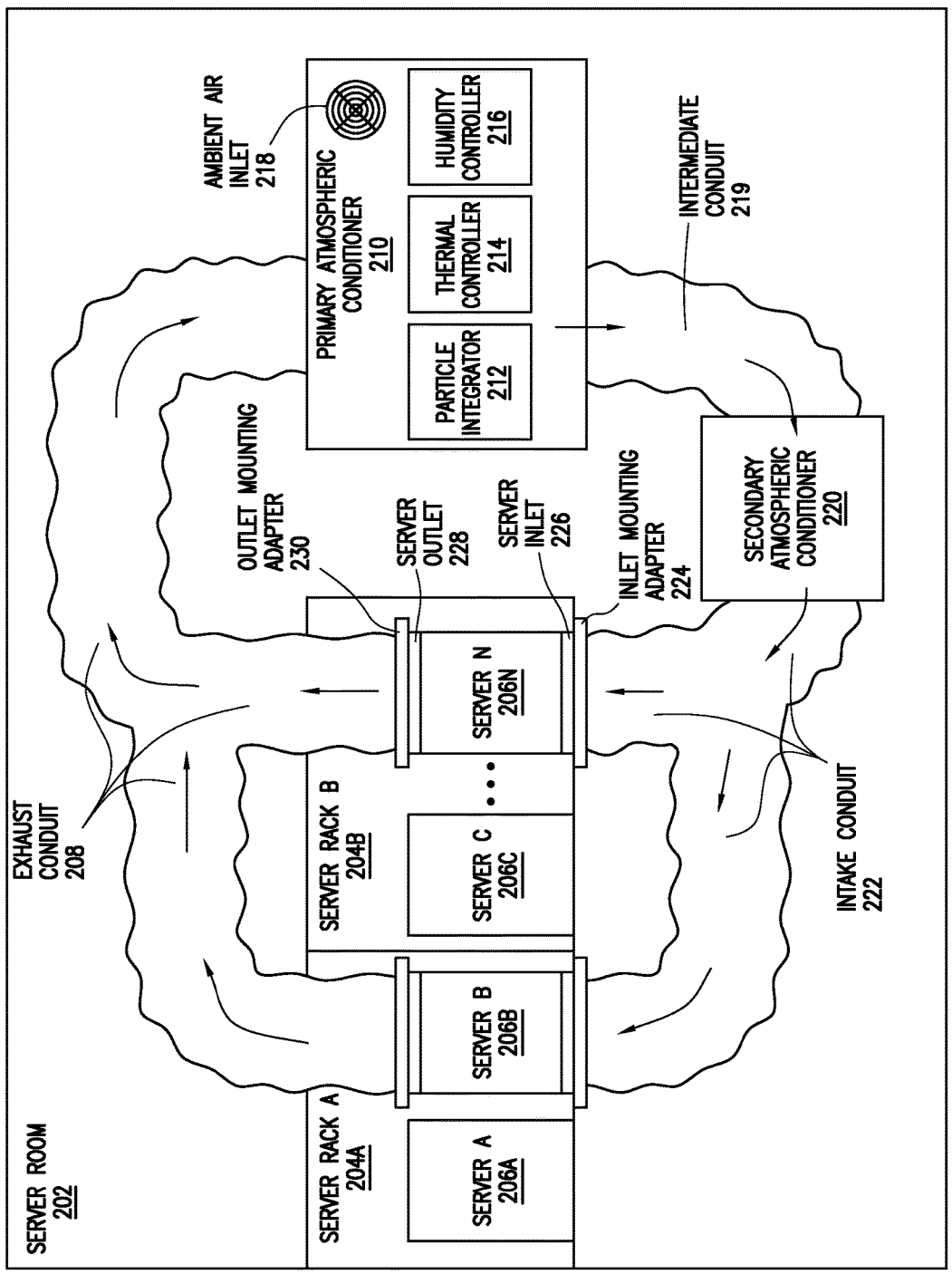
FIG. 2 shows a system for setting/controlling atmospheric conditions for multiple test computing devices in a facility also having a production computing device(s) in accordance with one or more embodiments of the invention in accordance with one or more embodiments of the invention.

FIG. 2 shows a system in accordance with one or more embodiments of the invention. As shown in FIG. 2, there exists a server room (202). The server room (202) is essentially the same as the server room (102) discussed above in reference to FIG. 1. One or more server racks (e.g., server rack A (204A), server rack B (204B)) in server room (202) are essentially the same as the one or more server racks (e.g., server rack A (104A), server rack B (104B)) discussed above in reference to FIG. 1. One or more servers (e.g., server A (206A), server B (206B), server C (206C), and server N (206N)) on the server racks are essentially the same as the one or more servers (e.g., server A (106A), server B (106B), server C (106C), server N (106N)) discussed above in reference to FIG. 1.

In FIG. 2, server B (206B) and server N (206N) are test computing devices. In other words, server B (206B) and server N (206N) are subjected to test air that has different atmospheric conditions (e.g., temperature, pressure, humidity, oxygen content, dust particles, etc.) than the air of the server room (202). The performance of server B (106B) and server N (106N) are observed, measured, evaluated, etc. while being exposed to the test air. Server A (206A) and server C (206C) are not under test and may be operating normally while exposed to the air of the server room (202). Accordingly, each of server A (206A) and server C (206C) may be referred to as a production computing device.

Still referring to FIG. 2, there exists a server outlet (228), a server inlet (226), an outlet mounting adapter (230), and an inlet mounting adapter (224). The server outlet (228), the server inlet (226), the outlet mounting adapter (230), and the inlet mounting adapter (224) are essentially the same as the server outlet (128), the server inlet (126), the outlet mounting adapter (130), and the inlet mounting adapter (124), discussed above in reference to FIG. 1. Like server N (206N), server B (206B) may also have and/or be connected to a server outlet, a server inlet, an outlet mounting adapter, and an inlet mounting adapter.

In one or more embodiments of the invention, the primary atmospheric conditioner (210), the ambient air inlet (218), the particle integrator (212), the thermal controller (214), and the humidity controller (216) are essentially the same as the primary atmospheric conditioner (110), the ambient air inlet (118), the particle integrator (112), the thermal controller (114), and the humidity controller (116) discussed above in reference to FIG. 1.

In one or more embodiments of the invention, the primary atmospheric conditioner (210) is connected to the exhaust conduit (208). Specifically, the exhaust conduit (208) branches, with one branch connecting to the server outlet of server B (206B) and the other branch connecting to the server outlet (228) of server N (206N). Except for the branching, the exhaust conduit (208) is essentially the same as the exhaust conduit (108), discussed above in reference to FIG. 1.

In one or more embodiments of the invention, the test air generated by the atmospheric conditioner(s) is delivered to server B (206B) and server N (206N) by an intake conduit (222). Specifically, the intake conduit (222) branches, with one branch connecting to the server inlet of server B (206B) and the other branch connecting to the server inlet (226) of server N (206N). Except for the branching, the intake conduit (222) is essentially the same as the intake conduit (122), discussed above in reference to FIG. 1.

In one or more embodiments of the invention, there also exists a secondary atmospheric conditioner (220). The secondary atmospheric conditioner is essentially the same as the secondary atmospheric conditioner (120), discussed in reference to FIG. 1. In one or more embodiments of the invention, the secondary atmospheric conditioner (220) is optional. However, when the secondary atmospheric conditioner (220) is present, it is connected to the primary atmospheric conditioner (210) by an intermediate conduit (219). The intermediate conduit (219) is essentially the same as the intermediate conduit (119) discussed in reference to FIG. 1.

While FIG. 2 shows a configuration of components, other configurations may be used without departing from the scope of the invention. For example, various components may be combined to create a single component. As another example, the functionality performed by a single component may be performed by two or more components. Further, although embodiments of the invention have focused heavily on severs (206A-206N), those skilled in the art, having the benefit of this detailed description, will appreciate that any type of computing device (e.g., personal computer (PC), laptop, mainframe, smart phone, personal digital assistant, cable box, kiosk, printer, tablet PC, e-reader, monitor, fax machine, copier, oscilloscope, electronic testing instrument, etc.) may also be used. Further still, although FIG. 2 only shows two test computing devices and thus two branches in the exhaust conduit (208) and the intake conduit (222), in other embodiments, any number of test computing devices, and thus any number of branches, may be present.

Figure 3:
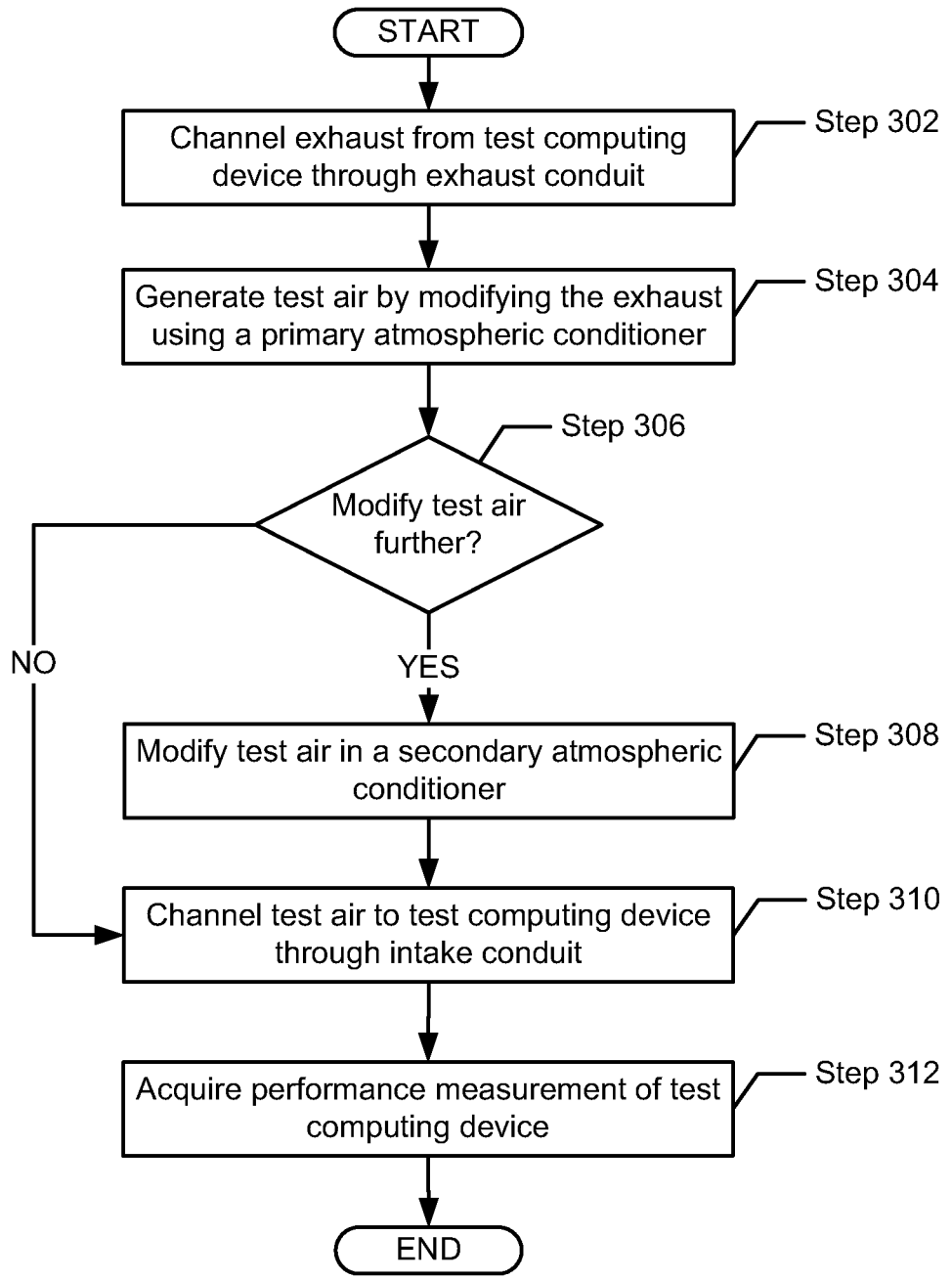
FIG. 3 shows a flowchart for setting/controlling atmospheric conditions for one or more test computing devices in accordance with one or more embodiments of the invention.

FIG. 3 shows a flowchart in accordance with one or more embodiments of the invention. The process depicted in FIG. 3 may be used to set/control the atmospheric conditions for one or more test computing devices. One or more of the steps in FIG. 3 may be performed by one or more of the components discussed above in reference to FIG. 1 and/or FIG. 2. Further, one or more of the steps shown in FIG. 3 may be omitted, repeated, and/or performed in a different order than the order shown in FIG. 3. Accordingly, the scope of the invention should not be considered limited to the specific arrangement of steps shown in FIG. 3.

Initially, exhaust expelled from the test computing device (e.g., server) is channeled through an exhaust conduit connected to the test computing device (Step 302). The exhaust conduit keeps the exhaust environmentally separated from the ambient air of the room in which the test computing device is situated (e.g., server room, datacenter) and any other computing devices that are in close proximity to the test computing device.

In Step 304, test air is generated by modifying the exhaust using a primary atmospheric conditioner in accordance with one or more embodiments of the invention. Specifically, the exhaust conduit is also connected to the primary atmospheric conditioner, and thus the exhaust conduit delivers the exhaust from test computing device to the primary atmospheric conditioner. Once exhaust enters the primary atmospheric conditioner from the exhaust conduit, the primary atmospheric conditioner may generate the test air by modifying the atmospheric conditions (e.g., temperature, moisture, pressure, etc.) of the exhaust. In one or more embodiment of the invention, users (i.e., server testers, network administrators, lab technicians, etc.) may use a user interface on the primary atmospheric conditioner to select (i.e., set, input, program, specify, etc.) the desired atmospheric conditions of the test air.

Continuing with Step 304, the primary atmospheric conditioner may modify the atmospheric conditions of the exhaust by modifying the temperature of the exhaust using a thermal controller. For example, the exhaust may be at a temperature of 85° F. To generate test air with a temperature of 95° F., the temperature controller heats the exhaust until a temperature of 95° F. is reached.

Continuing with Step 304, the primary atmospheric conditioner may generate test air by modifying the moisture content of the exhaust using a humidity controller. For example, the exhaust may have a moisture content of 10%. To generate test air with a moisture content of 40%, the humidity controller adds moisture to the exhaust until a moisture content of 40% is reached. Further, the primary atmospheric conditioner may generate test air by introducing dust particles into the exhaust. For example, the dust particles in the exhaust may be 50 μg/m$^3$. To generate test air with 200 μg/m$^3$ of dust particles, the particle integrator may release dust into the exhaust until a measurement of 200 μg/m$^3$ is attained.

Continuing with Step 304, the primary atmospheric conditioner may generate test air by modifying pressure of the exhaust. In one or more embodiments of the invention, the primary atmospheric conditioner may include fans to accelerate or decelerate the exhaust. For example, the exhaust has a pressure of 100 kPa. To generate test air with a pressure of 50 kPa, fans that flow against the flow of the exhaust may be used to decelerate the exhaust to reduce pressure of the exhaust to 50 kPa. Finally, the primary atmospheric conditioner may generate test air by modifying the composition of gases in the exhaust. For example, the exhaust is composed of 21% oxygen. To generate the test air with 40% oxygen, oxygen may be added (e.g., by accessing an oxygen tank or store). In one or more embodiments of the invention, a combination of the mechanisms to modify atmospheric conditions of the exhaust may be used to generate test air. For example, moisture content and temperature may be modified to generate test air.

In Step 306, it is determined whether the test air should be modified further in accordance with one or more embodiments of the invention. In one or more embodiments of the invention, the test air should be modified further if the test air outputted by the primary atmospheric conditioner has not attained the desired atmospheric conditions for testing (e.g., as set by a user using a user interface on the primary atmospheric conditioner). For example, consider a scenario in which test air should be 50° F. If temperature of the exhaust is cooled from 88° F. to 70° F. using the primary atmospheric conditioner, the test air has not cooled to 50° F. An additional (e.g., secondary) atmospheric conditioner is needed to further cool the test air to 50° F. When it is determined that the test air should be modified further, the process proceeds to Step 308. When it is determined that the test air does not need to be modified further, the process proceeds to Step 310.

In Step 308, test air is modified using a secondary atmospheric conditioner in accordance with one or more embodiments of the invention. The secondary atmospheric conditioner may modify the test air that has been outputted by the primary atmospheric conditioner using essentially the same mechanisms of the primary atmospheric conditioner described above in Step 304 (e.g., modify temperature using thermal controller, modify moisture content using humidity controller, introduce dust particles using particle integrator, etc.). The primary atmospheric conditioner and the second atmospheric conditioner may be linked by an intermediate conduit. The intermediate conduit delivers the test air that has been outputted by the primary atmospheric conditioner to the secondary atmospheric conditioner.

In one or more embodiments of the invention, the secondary atmospheric conditioner does not modify the atmospheric conditions of the exhaust. In such embodiments, the secondary atmospheric conditioner may be used to propel the test air from the primary atmospheric conditioner to the inlet of the test computing device.

In Step 310, test air is channeled to the test computing device through an intake conduit in accordance with one or more embodiments of the invention. The test air that exits from the secondary atmospheric conditioner or the primary atmospheric conditioner (if a secondary atmospheric conditioner is not used) enters the intake conduit. The intake conduit keeps the test air environmentally separated from the ambient air of the room in which the test computing device is situated and environmentally separated from any other computing device in close proximity to the test computing device. In one or more embodiments of the invention, additional devices (e.g., fans) within the intake conduit may be used to propel the test air from either the secondary atmospheric conditioner (if used) or the primary atmospheric conditioner to the test computing device.

In Step 312, a performance measurement of the test computing device is acquired in accordance with one or more embodiments of the invention. The performance measurement may correspond to the speed of the test computing device, the number of calculations performed by the test computing device, the heat generated by the test computing device, or any metric that describes the function of any software and/or hardware of the test computing device. The performance measurement may be acquired by an electronic testing instrument connected to the test computing device. In one or more embodiments of the invention, the performance measurement of the test computing device is acquired once the test computing device is exposed to the test air.

Figure 4:
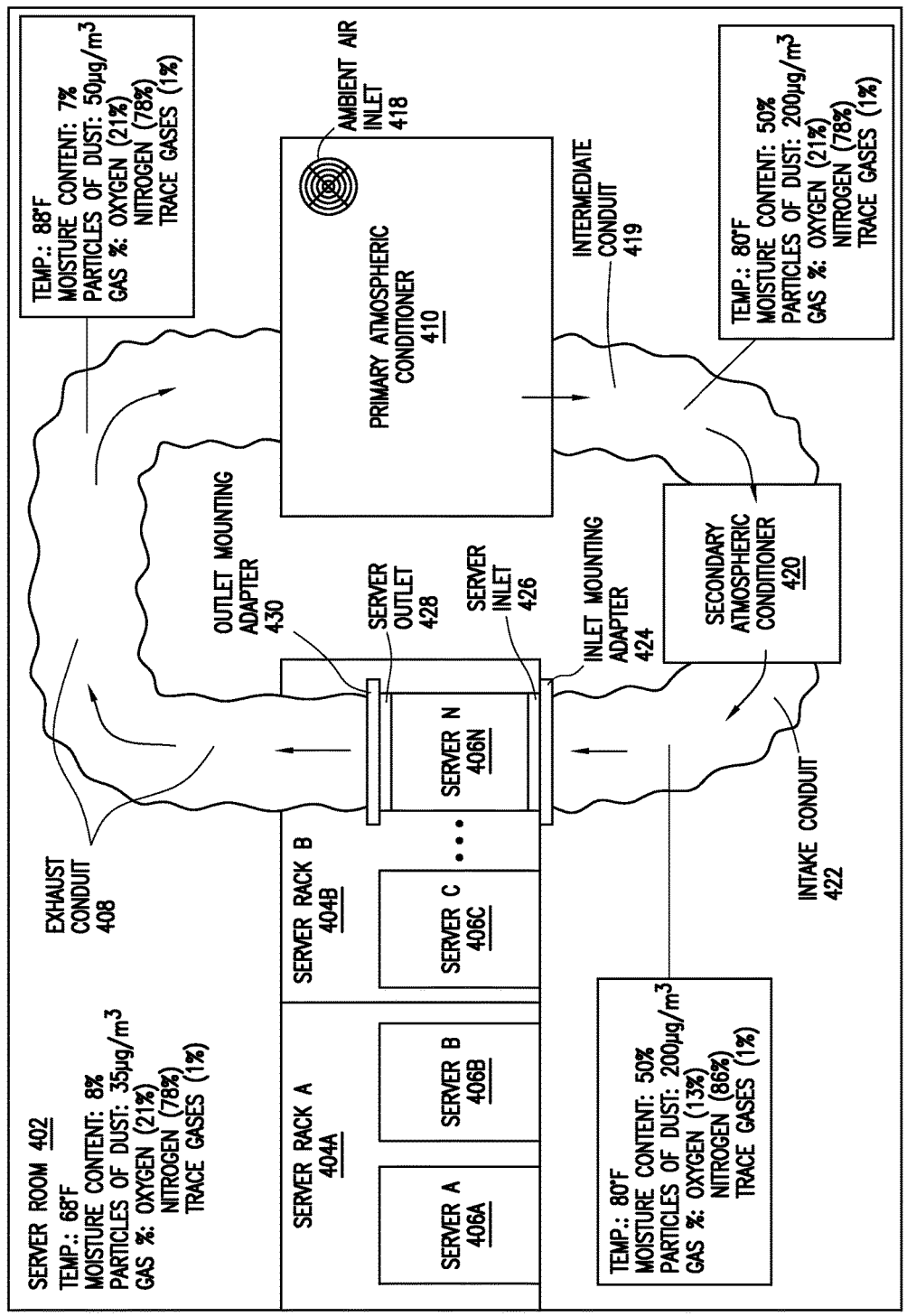
FIG. 4 shows an example of setting/controlling atmospheric conditions for a test computing device in accordance with one or more embodiments of the invention.

FIG. 4 shows an example in one or more embodiments of the invention. The following example is for explanatory purposes only and not intended to limit the scope of the invention.

Referring to FIG. 4, consider a scenario in which ambient air in a server room (402) has the following atmospheric conditions: temperature of 68° F., moisture content of 8%, 35 µg/m$^3$ particles of dust, and gas percentages of 21% oxygen, 78% nitrogen, and 1% trace gases. The server room (402) includes one or more servers (e.g., server A (406A), server B (406B), server C (406C), and server N (406N)). Server A (406A) and server B (406B) are mounted on server rack A (404A). Server C (406C) and server N (406N) are mounted on server rack B (404B). Server A (406A), server B (406B), and server C (406C) are production computing devices operating in the ambient air of the server room (402). Server N (406N) is a test computing device receiving atmospheric conditions that differ from the ambient air in the server room (402).

The server outlet (428) of server N (406N) is connected to an exhaust conduit (408) using an outlet mounting adapter (430). Exhaust from server N (406N) is channeled through the exhaust conduit (408). The exhaust in the exhaust conduit (408) has the following atmospheric conditions: temperature of 88° F., moisture content of 7%, 50 µg/m$^3$ particles of dust, and gas percentages of 21% oxygen, 78% nitrogen, and 1% trace gases. The temperature of the exhaust is higher (88° F.) compared to the ambient air (68° F.) due to heat produced by server N (406N). The atmospheric conditions in the exhaust conduit differ from the ambient air. Moreover, the exhaust conduit (408) environmentally separates the exhaust from the ambient air and the other servers (406A-406C).

Continuing with the example in FIG. 4, the exhaust then enters a primary atmospheric conditioner (410). The ambient air inlet (418) is set to allow the intake of ambient air into the primary atmospheric conditioner (410) to mix with the exhaust. The primary atmospheric conditioner modifies the exhaust to generate the test air. The intermediate conduit (419) channels test air from the primary atmospheric conditioner to the secondary atmospheric conditioner. The test air in the intermediate conduit (419) has the following atmospheric conditions: temperature of 80° F., moisture content of 50%, 200 µg/m$^3$ particles of dust, and gas percentages of 21% oxygen, 78% nitrogen, and 1% trace gases. The ambient air inlet (418) cooled the temperature of the exhaust from 88° F. to 80° F. The humidity controller in the primary atmospheric conditioner (410) increased the moisture content of the exhaust from 7% to 50%. Finally, the particle integrator in the primary atmospheric conditioner (410) introduced dust particles to reach 200 µg/m$^3$. The test air in the intermediate conduit has different atmospheric conditions to the exhaust in the exhaust conduit (408) and to the ambient air in the server room (402). The intermediate conduit (419) keeps the test air environmentally separated from the ambient air and the other servers (406A-406C).

The test air from the intermediate conduit (419) enters a secondary atmospheric conditioner (420). The test air modified by the secondary atmospheric conditioner then enters an intake conduit (422). The test air in the intake conduit (422) has the following atmospheric conditions: temperature of 80° F., moisture content of 50%, 200 µg/m$^3$ particles of dust, and gas percentages of 13% oxygen, 86% nitrogen, and 1% trace gases. The secondary atmospheric conditioner (420) modified the test air from the intermediate conduit (419) by increasing the level of nitrogen gas in the test air and decreasing the level of oxygen. The test air in the intake conduit (422) is connected to a server inlet on server N (406N) using an inlet mounting adapter (424). The test air may then flow into server N (406N). Thus, server N (406N) is exposed to the atmospheric conditions of the test air from the intake conduit (422).

Continuing with the example in FIG. 4, while server N (406N) is exposed to the test air described above, the production computing devices in the server room (402) (e.g., server A (406A), server B (406B), and server C (406C)) are not exposed to the test air. The production computing devices are operating in the ambient air in the server room (402) described above.

Embodiments of the invention enable the control of atmospheric conditions within one or more test computing devices in a room that also includes one or more production computing devices. Embodiments of the invention channel test air to the test computing device and isolate the test air from the production computing devices. Therefore, embodiments of the invention prevent disruption of the production computing devices by the test air.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system for controlling an atmospheric condition, comprising:
    an exhaust conduit, external to a first test computing device, configured to channel exhaust from the first test computing device;
    a primary atmospheric conditioner, external to the first test computing device, configured to generate test air comprising the atmospheric condition for the first test computing device by modifying the exhaust, wherein the primary atmospheric conditioner comprises a particle integrator configured to introduce a plurality of dust particles into the exhaust; and
    an intake conduit, external to the first test computing device, configured to channel the test air to the first test computing device.

2. The system of claim 1, further comprising:
    an inlet mounting adapter configured to connect an inlet of the first test computing device to the intake conduit; and
    an outlet mounting adapter configured to connect an outlet of the first test computing device to the exhaust conduit.

3. The system of claim 1, further comprising:
    a secondary atmospheric conditioner configured to modify the test air.

4. The system of claim 1, wherein the primary atmospheric conditioner comprises:
    a thermal controller configured to modify a temperature of the exhaust;
    a humidity controller configured to modify a moisture content of the exhaust; and
    an ambient air inlet configured to intake ambient air to mix with the exhaust.

5. The system of claim 1, wherein the atmospheric condition comprises at least one selected from a group consisting of a temperature, a plurality of dust particles, a moisture content, a pressure, and a composition of a plurality of gases.

6. The system of claim 1, wherein the exhaust conduit is further configured to channel exhaust from a second test computing device to the primary atmospheric conditioner.

7. The system of claim 6, wherein the intake conduit is further configured to channel the test air to the second test computing device.

8. A system for controlling an atmospheric condition, comprising:
a plurality of production computing devices in a room;
a first test computing device in the room;
an exhaust conduit, external to the first test computing device, configured to:
channel exhaust from the first test computing device; and
isolate the plurality of production computing devices from the exhaust of the first test computing device;
a primary atmospheric conditioner, external to the first test computing device and the plurality of production computing devices, configured to generate test air comprising the atmospheric condition for the first test computing device by modifying the exhaust; and
an intake conduit, external to the first test computing device, configured to:
channel the test air to the first test computing device; and
isolate the plurality of production computing devices from the test air.

9. The system of claim 8, further comprising:
an inlet mounting adapter configured to connect an inlet of the first test computing device to the intake conduit; and
an outlet mounting adapter configured to connect an outlet of the first test computing device to the exhaust conduit.

10. The system of claim 8, further comprising:
a secondary atmospheric conditioner configured to modify the test air.

11. The system of claim 8, wherein the primary atmospheric conditioner comprises:
a particle integrator configured to introduce a plurality of dust particles to the exhaust;
a thermal controller configured to modify a temperature of the exhaust;
a humidity controller configured to modify a moisture content of the exhaust; and
an ambient air inlet configured to intake ambient air to mix with the exhaust.

12. The system of claim 8, wherein the atmospheric condition comprises at least one selected from a group consisting of a temperature, a plurality of dust particles, a moisture content, a pressure of the exhaust, and a composition of a plurality of gases in the exhaust.

13. The system of claim 8, wherein the exhaust conduit is further configured to:
channel exhaust from a second test computing device to the primary atmospheric conditioner; and
isolate the plurality of production computing devices from the exhaust of the second test computing device.

14. The system of claim 13, wherein the intake conduit is further configured to channel the test air to the second test computing device.

15. A method for controlling an atmospheric condition, comprising:
channeling, by an exhaust conduit external to a first test computing device, exhaust from the first test computing device;
generating, by a primary atmospheric conditioner external to the first test computing device, test air comprising the atmospheric condition by modifying the exhaust, wherein the primary atmospheric conditioner comprises a particle integrator configured to introduce a plurality of dust particles to the exhaust; and
channeling, by an intake conduit external to the first test computing device, the test air to the first test computing device.

16. The method of claim 15, further comprising:
channeling exhaust from a second test computing device to the primary atmospheric conditioner.

17. The method of claim 16, further comprising:
channeling the test air to the second test computing device.

18. The method of claim 15, further comprising:
modifying the test air by a secondary atmospheric conditioner.

19. The method of claim 15, further comprising:
acquiring a performance measurement of the first test computing device receiving the test air, wherein the performance measurement is selected from a group consisting of the speed of the test computing device, the number of calculations performed by the test computing device, and the heat generated by the test computing device.

20. The method of claim 15, wherein the primary atmospheric conditioner comprises:
a thermal controller configured to modify a temperature of the exhaust;
a humidity controller configured to modify a moisture content of the exhaust; and
an ambient air inlet configured to intake ambient air to mix with the exhaust.

* * * * *